(12) United States Patent
Framroze

(10) Patent No.: US 7,498,431 B2
(45) Date of Patent: *Mar. 3, 2009

(54) PROCESS FOR THE PREPARATION OF CHIRAL AZETIDINONES

(76) Inventor: Bomi Patel Framroze, 3 Shree Sadan, 4/A Carmichael Road, Mumbai, Maharashtra (IN) 400026

( * ) Notice: Subject to any disclaimer, the term of this patent is extended or adjusted under 35 U.S.C. 154(b) by 452 days.

This patent is subject to a terminal disclaimer.

(21) Appl. No.: 11/291,236

(22) Filed: Dec. 1, 2005

(65) Prior Publication Data

US 2007/0129540 A1 Jun. 7, 2007

(51) Int. Cl.
*C07D 205/08* (2006.01)
*C07C 309/66* (2006.01)

(52) U.S. Cl. .............................. 540/200; 560/60; 558/52
(58) Field of Classification Search ................... 540/200
See application file for complete search history.

(56) References Cited

U.S. PATENT DOCUMENTS

| 5,856,473 | A | 1/1999 | Shankar |
| 6,207,822 | B1 | 3/2001 | Thiruvengadam et al. |
| 7,002,008 | B2 | 2/2006 | Framroze |
| 2004/0254369 | A1 | 12/2004 | Framroze |

*Primary Examiner*—Mark L Berch
(74) *Attorney, Agent, or Firm*—Altimatia, LLC; David M. Gange

(57) ABSTRACT

Processes for preparing compounds of formula I are disclosed comprising the steps of:

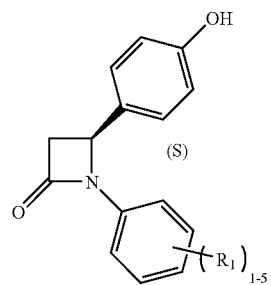

(a) forming of chiral propionic acid ester compounds of formula V.

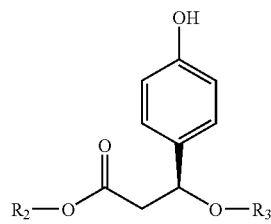

(b) reacting compounds of formula V with aniline compounds to yield compounds of formula I.

18 Claims, No Drawings

PROCESS FOR THE PREPARATION OF CHIRAL AZETIDINONES

FIELD

Embodiments of the invention relate to processes for the preparation of chiral substituted azetidinones.

BACKGROUND

Embodiments of the invention relate to processes for preparing chiral azetidinones, such as 1-(4-fluorophenyl)-4(S)-(4-hydroxyphenyl)-azetidin-2-one, a compound useful as an intermediate in the preparation of hypocholesterolemic agents, and to the preparation of substituted carboxy and sulfonyloxy propionic acid esters, intermediates useful in the above mentioned process.

WO 95/08532 discloses a series of hypocholesterolemic agents comprising 3-hydroxypropyl azetidinones and describes several processes suitable for preparing these azetidinones. WO 93/02048 discloses a process to stereoselectively prepare 3- and 4-substituted azetidinones by cyclization of beta-amino amides. WO 95/08532 and WO 97/45406 disclose a method to prepare 3- and 4-substituted azetidinones by reacting 4-phenylbutyrolactones and 4-methoxybenzylideneaniline. WO 97/16424 discloses a method to prepare the desired 3- and 4-substituted azetidinones by reacting 4-fluorocinnamyl bromide and a lactam.

More recently U.S. Pat. No. 6,207,882 describes a process to generate 3- and 4-substituted azetidinones stereoselectively using p-fluorobenzoylbutyric acid and chiral 4-phenyloxazolidon-2-ones. U.S. Pat. No. 5,886,171 had also previously described a stereoselective process to the desired azetidinones starting from 3(S)-hydroxy-gamma-lactone. U.S. Pat. No. 6,133,001 describes an enzymatic microbial reduction of a 3-keto azetidinone. Other methods exist in the prior art which teach to process of converting the 3-unsubstituted azetidinone, which is the subject of this patent, into 3-, and 4-substituted azetidinone hypocholesterolemic agents, such as by the method described in U.S. Pat. No. 5,856,473.

Related processes may also be found in US Patent Application Publication Number 2004/0254369 A1, which corresponds to U.S. patent application Ser. No. 10/460,877. The references discussed within this application are hereby incorporated herein by reference.

SUMMARY

Embodiments of the invention provide novel processes for preparing compounds of formula I.

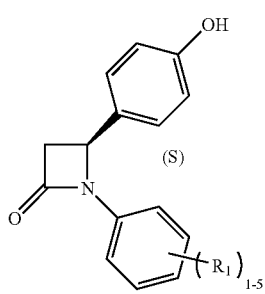

comprising:

(a) preparing a chiral propionic acid of formula III, making its ester IV, and activating its aliphatic hydroxy group to give a compound of formula V.

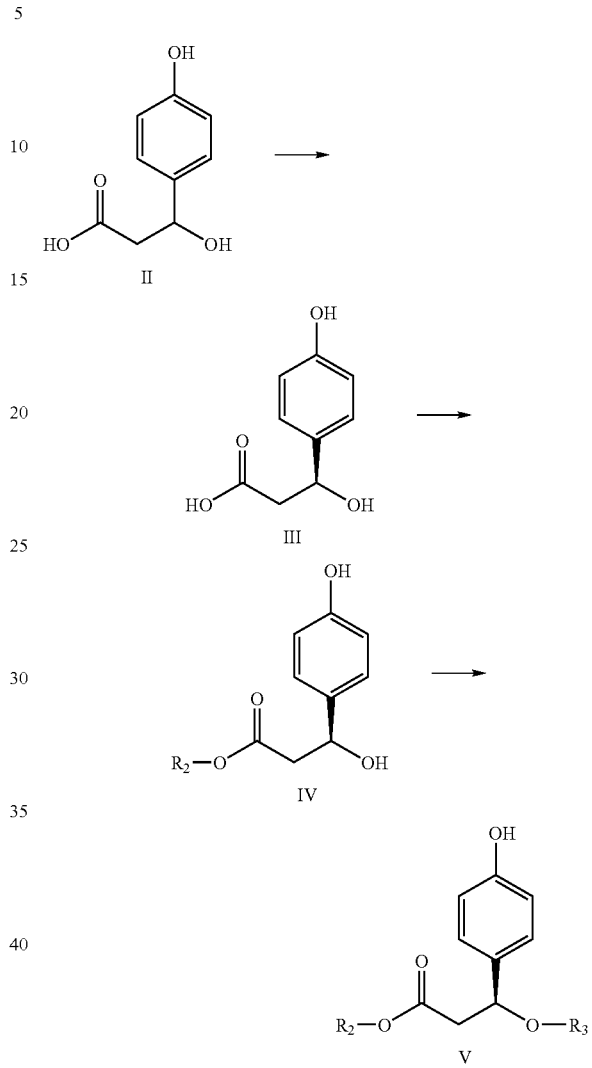

(b) reacting the compound of formula V with an aniline to give an azetidinone compound of formula I Embodiments of the invention relate more particularly to step (b), wherein the compound of formula V is cyclized, in the presence of sodium iodide, with an aniline to yield an azetidinone compound of formula I. $R_1$ may be one or more instances of H, F, Cl, Br, I, $C_1$-$C_6$ alkyl, O—$C_1$-$C_6$ alkyl, N—($C_1$-$C_6$ alkyl)$_2$, S—$C_1$-$C_6$ alkyl, aryl, and O-aryl. $R_2$ may be $C_1$-$C_6$ alkyl. $R_3$ may be alkyl sulfonyl, aryl sulfonyl, or alkyl carbonyl. If $R_2$ is methyl then $R_3$ is not methanesulfonyl.

The processes described herein are novel methods to stereospecifically generate 4-substituted azetidinones, compared to the procedures described in the prior art. More specifically the processes of the invention, compared to the procedures for preparing compounds of formula I disclosed in the prior art, are simpler procedures, involving mild reagents and starting materials, which are commonly available in commercially accessible quantities and having an improved overall yield. The compounds of formula I are produced with greater efficiency in a highly stereoselective manner

DETAILED DESCRIPTION

The syntheses begin by obtaining 3(S)-(4-hydroxyphenyl)-3-hydroxy-propionic acid, compound III. Chiral propionic acid III may be obtained by chiral synthesis or by resolution of the corresponding racemic propionic acid. For example, 3(S)-(4-methoxyphenyl)-3-hydroxy-propionic acid may be synthesized by exposing 4-methoxybenzaldehyde to the reactive species formed by exposing bromoacetic acid L-menthol ester to 9:1 zinc/copper as described in *J. Org. Chem.*, 16, (1951), 728.

Alternatively, racemic 3-(4-hydroxyphenyl)-3-hydroxypropionic acid II (La Manna, Farmaco Ed. Sci. Vol. 19, Pg 506, 1964) may be resolved to give the chiral propionic acid III. Resolution may be accomplished in a variety of ways including chromatography using chiral chromatographic media, by esterification with chiral alcohols followed by separation of the resulting diastereomers followed by hydrolysis to III, and by fractional crystallization of chiral amine salts. Useful chiral amines include (+)-2-amino-1-butanol and (−) alpha methyl benzylamine.

The next step comprises making an ester of compound III. Acidic conditions such as 5% alcoholic HCl, or para-toluenesulfonic acid in refluxing alcohol may also be used to prepare esters IV. Alkyl esters comprising $R_2$ equal to methyl, ethyl, propyl, isopropyl, butyl and pentyl and others may be prepared.

The next step comprises activating the alkyl hydroxy group of IV by contacting compound IV with an activating agent to form V wherein $R_3$ is selected from the group consisting of alkylcarbonyl, alkylsulfonyl and arylsulfonyl. If $R_2$ is methyl then $R_3$ is not methanesulfonyl. Compound V may be formed by exposing compound IV to anhydrides such as acetic acid anhydride or para-toluenesulfonic acid anhydride in the presence of base such as triethylamine, pyridine, or other amine bases. Other anhydrides may be used including propionic acid anhydride, butyric acid anhydride, pentanoic acid anhydride, hexanoic acid anhydride, methanesulfonic acid anhydride, benzenesulfonic acid anhydride, and para-bromobenzene sulfonic acid anhydride. In addition, compound V may be formed by exposing compound IV to acid halides such as para-toluenesulfonyl chloride or methanesulfonyl chloride. Other acid halides may be used including acetyl halides, propionic acid halides, butyric acid halides, pentanoic acid halides, hexanoic acid halides, methanesulfonic acid halides, benzenesulfonic acid halides, para-bromobenzene sulfonic acid halides, and para-toluenesulfonic acid halides. Specific acid halides and acid anhydrides that may be used include acetyl chloride, acetyl bromide, acetic acid anhydride, propionyl chloride, propionic acid anhydride, butanoyl chloride, butanoic acid anhydride, pentanoyl chloride, pentanoic acid anhydride, methanesulfonyl chloride, methanesulfonic acid anhydride, para-toluenesulfonyl chloride, para-toluenesulfonic acid anhydride, benzenesulfonyl chloride, benzenesulfonic acid anhydride, para-bromobenzenesulfonyl chloride, para-bromobenzene sulfonic anhydride, ethanesulfonyl chloride, and ethanesulfonic acid anhydride. Other chemically similar acid chlorides and anhydrides may also be used.

The final step comprises reacting an activated 3(S)-(4-hydroxyphenyl)-3-hydroxy-propionic acid ester derivative V with an aniline in the presence of alkali halide to form a compound of formula I wherein $R_1$ is at least one substituent selected from the group consisting of H, halogen, alkyl, O-alkyl, N-dialkyl, S-akyl, aryl, and O-aryl. In the cyclization step to form compounds of formula I, a compound of formula V and an aniline are dissolved in solvent comprising one or more solvents selected from the group consisting of acetone, 2-butanone, p-dioxane, acetonitrile, tetrahydrofuran, and any other suitable aprotic polar solvent, and 1% to 10% mol/mol of sodium iodide or other alkali halide is added to the solution at room temperature. The mixture is refluxed until the reaction is complete, providing a desired azetidinone compound of formula I. Suitable aniline substituents include H, halogen, alkyl, alkoxy, dialkylamino, S-alkyl, aryl, O-aryl, and S-aryl. Electron donating substituents are preferred.

As used herein 'alkyl' refers to saturated carbon-hydrogen containing groups, including straight chain, branched chain, and cyclic groups such as methyl, ethyl, propyl, iso-propyl, cyclopropyl, butyl, iso-butyl, tert-butyl, cyclobutyl and the like containing from one to six carbon atoms.

As used herein 'alkyloxy' or 'alkoxy' refers to alkyl groups to which an oxygen atom is attached. Representative groups include methoxy, ethoxy, propoxy, isopropoxy, cyclopropoxy, butoxy, isobutoxy, tertbutoxy, cyclobutoxy and the like containing from one to six carbon atoms.

As used herein 'dialkylamino' refers to amino groups to which two alkyl groups have been attached. The alkyl groups may be the same or they may be different from one another, and may contain from one to six carbon atoms.

As used herein 'S-alkyl' refers to alkyl groups to which a sulfur atom is attached. Representative groups include S-methyl, S-ethyl, S-propyl, S-isopropyl, S-cyclopropyl, S-butyl, S-isobutyl, S-tertbutyl, S-cyclobutyl, and the like containing from one to six carbon atoms.

As used herein 'aryl' refers to aromatic compounds satisfying the 4n+2 Hückel rule for aromaticity. Aryl includes heteroaryl as well as carbon aryl. Aryl groups may in turn be substituted with one or more substituents including H, halogen, alkyl, alkoxy, dialkylamino, and S-alkyl.

As used herein 'O-aryl' refers to aryl groups to which an O is attached.

As used herein 'S-aryl' refers to an aryl group to which an S is attached.

As used herein 'alkylcarbonyl' refers to a group comprising an alkyl group, or substituted alkyl group, and a carbonyl group. Examples include, but are not limited to, the acetyl, propionyl, butyryl groups, trifluoroacetyl, trifluoropropionyl, pentafluoropropionyl, trichloroacetyl, and chloroburyryl groups.

As used herein 'alkylsulfonyl' refers to a group comprising an alkyl group, or substituted alkyl group, and a sulfonyl group. Examples include, but are not limited to, methanesulfonyl, trifluoromethanesulfonyl, ethanesulfonyl, pentafluoroethanesulfonyl, propanesulfonyl, butanesulfonyl, isopropanesulfonyl, and pentanesulfonyl.

As used herein 'arylsulfonyl' refers to a group comprising an aryl group, or substituted aryl group, and a sulfonyl group. Examples include, but are not limited to, benzenesulfonyl, para-bromobenzenesulfonyl, para-chlorobenzenesulfonyl, toluenesulfonyl, dimethylbenzenesulfonyl, fluorobenzenesulfonyl, and ethylbenzenesulfonyl.

EXPERIMENTAL RESULTS

Example 0

To a clean dry 250 ml round bottomed flask equipped with a magnetic stirrer and reflux condenser was added 15.6 g of L-menthol (1R,2S,5R)(−)-menthol in 100 ml of water and 4 g of NaOH flakes and the mixture refluxed for 4 hours. The water was removed by distillation to yield a pale yellow crystalline solid (sodium salt of L-menthol) which was dried in an oven at 90 degrees C. overnight and used as is in the next step. To the dry solid from above was added 100 ml of dry toluene to form a suspension and to this stirred suspension was added 20 g of bromo acetyl bromide and the mixture stirred at RT for 10 hours during which time the reaction becomes a clear yellow solution with a faint brown precipitate. The reaction was filtered and the filtrate was added to a fresh 250 ml RBF equipped with a magnetic stirrer and reflux condenser. To this reaction was added 10 gms of 9:1 zinc-copper pellets (prepared as per the procedure described in J. Org. Chem. 16, (1951), 728) and 4 g of 4-methoxybenzaldehyde and the mixture set to reflux. Upon reflux 100 mg of cupric chloride was added ($CuCl_2.2H_2O$). The mixture was refluxed for 3 hours and then 50 ml of toluene was removed by distillation. The remaining solution was placed in a separatory funnel and 50 ml of 1N NaOH was added, and the acid was extracted into the aqueous layer. The organic layer was discarded, fresh toluene was added, and the aqueous layer was acidified with 2N HCl. The organic layer was collected and the solvent was removed to yield 4.1 g of a yellow solid identified as 3(S)-(4-methoxyphenyl)-3-hydroxy-propionic acid.

1H NMR (d-DMSO)-d7.41, d, 2H; d6.94, d, 2H; d3.97, broadpeak, 2H; d3.78, s, 3H; d3.23, d, 1H; d2.14, dd, 2H. Rotation-MeOH=−22.4

Example 1

To 14.6 gm of compound II and 8 gm of (+)-2-amino-1-butanol was added 150 ml of 2:1 solution of ethanol and water near its boiling point until dissolution just occurs. After cooling the precipitated salt was collected and dried to yield 13.1 gm of 3(S)-(4-hydroxyphenyl)-3-hydroxy propionic acid butanol amine salt with >92% ee (enantiomeric excess). The salt was added to a solution of 400 ml of 5% hydrochloric acid in methanol and refluxed for 2 hours and the methanol evaporated under vacuum. 200 ml of methylene chloride and 200 ml of water was added to the residue and the layers separated. The organic layer was evaporated to yield 12.9 gm of 3(S)-(4-hydroxyphenyl)-3-hydroxy propionic methyl ester (IVa) which was dissolved in 100 ml of THF and to it was added 9.2 gm of methanesulfonyl chloride and 28 ml of triethylamine. The solution was allowed to stir at 35 degrees C. for 2 hours, cooled and evaporated to near dryness. To this residue was added 100 ml of methylene chloride and 100 ml of water and the layers separated. The organic layer was washed with 1N hydrochloric acid and saturated sodium bicarbonate, separated, dried over sodium sulfate and evaporated to yield 14.1 gm of a compound of formula Va.

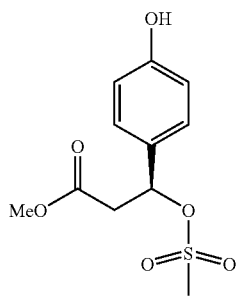

Va $^1$H NMR δ7.56, d, 2H; δ7.36, d, 2H; δ4.21, dd, 1H; δ3.61, s, 3H; δ3.34, s, 3H; δ2.01, t, 2H.

Example 2

To 25.9 gm of the compound of formula Va dissolved in 250 ml of acetone was added 11.1 gm of 4-fluoroaniline and 7 gm of sodium iodide. The mixture was refluxed for 8 hours and the acetone was removed under vacuum. To the residue was added 200 ml of ethyl ether and washed with saturated sodium bicarbonate, water, separated and evaporated to yield 22.4 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H.

Example 3

To 14.6 gm of compound II and 10.9 gm of (−)-alpha methyl benzylamine was added 200 ml of methyl isobutyl ketone near its boiling point until dissolution just occurs. After cooling, the precipitated salt was collected and dried to yield 13.1 gm of 3(S)-(4-hydroxyphenyl)-3-hydroxy-propionic acid benzyl amine salt with 93% ee (enantiomeric excess). The salt was added to a solution of 400 ml of 5% hydrochloric acid in methanol and refluxed for 2 hours and the solvent evaporated at 20 mm vacuum. 200 ml of ethyl acetate and 200 ml of water was added to the residue and the layers separated. The organic layer was evaporated to yield 13.8 gm of 3(S)-(4-hydroxyphenyl)-3-hydroxy-propionic acid methyl ester (IVa) which was dissolved in 100 ml of THF and to it was added 9.8 gm of methane sulfonyl chloride and 30 ml of triethylamine. The solution was allowed to stir at 35 degrees C. for 2 hrs, cooled and evaporated to near dryness. To this residue was added 100 ml of ethyl acetate and 100 ml of water and the layers separated. The organic layer was washed with 1N hydrochloric acid and saturated sodium bicarbonate, separated, dried over sodium sulfate and evaporated to yield 14.3 gm of a compound of formula Va.

Example 4

To 14.6 gm of compound of formula II and 8 gm of (+)-2-amino-1-butanol was added 150 ml of 2:1 solution of ethanol and water near its boiling point until dissolution just occurs. After cooling, the precipitated salt was collected and dried to yield 13.1 gm of 3(S)-(4-hydroxyphenyl)-3-hydroxy-propionic acid butanol amine salt with 92% ee (enantiomeric excess). The salt was added to a solution of 250 ml of 2 gm para-toluenesulfonic acid in ethanol and refluxed for 2 hours and the solvent evaporated under vacuum. 200 ml of diethyl ether and 200 ml of water was added to the residue and the layers separated. The organic layer was evaporated to yield 8.1 gm of 3(S)-(4-hydroxyphenyl)-3-hydroxy-propionic acid ethyl ester IVb.

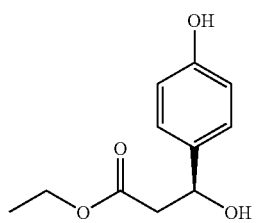

IVb $^1$H NMR (d-DMSO)-δ7.61, d, 2H; δ7.09, d, 2H; δ4.13, bm, 3H; δ3.62, q, 2H; δ1.94, t, 2H; δ1.14, t, 3H.

Example 5

Compound IVb (13.9 grams) was dissolved in 150 ml of THF and to it was added 9.9 gm of methane sulfonyl chloride and 32 ml of triethylamine. The solution was allowed to stir at 50 degrees C. for 2 hrs, cooled and evaporated to near dryness. To this residue was added 100 ml of ethyl acetate and 100 ml of water and the layers separated. The organic layer was washed with 1N hydrochloric acid and saturated sodium bicarbonate, separated, dried over sodium sulfate and evaporated to yield 13.9 gm of a compound of formula Vb.

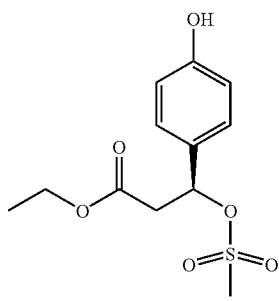

Vb

Example 6

To 14.6 gm of compound II and 8 gm of (+)-2-amino-1-butanol was added 150 ml of 2:1 solution of ethanol and water near its boiling point until dissolution just occurs. After cooling, the precipitated salt was collected and dried to yield 13.7 gm of 3(S)-(4-hydroxyphenyl)-3-hydroxy-propionic acid butanol amine salt with 95% ee (enantiomeric excess). The salt was added to a solution of 200 ml of 5% hydrochloric acid in methanol and refluxed for 2 hours and the methanol evaporated under vacuum. 200 ml of methylene chloride and 200 ml of water was added to the residue and the layers separated. The organic layer was evaporated to yield 13.5 gm of 3(S)-(4-hydroxyphenyl)-3-hydroxy-propionic methyl ester (IVa) which was dissolved in 100 ml of p-dioxane and to it was added 15.3 gm of para-toluenesulfonyl chloride and 30 ml of pyridine. The solution was allowed to stir at room temperature for 3 hrs, cooled and evaporated to near dryness. To this residue was added 100 ml of methylene chloride and 300 ml of water and the layers separated. The organic layer was washed with 1N hydrochloric acid and saturated sodium bicarbonate, separated, dried over sodium sulfate and evaporated to yield 9.0 gm of a compound of formula Vc.

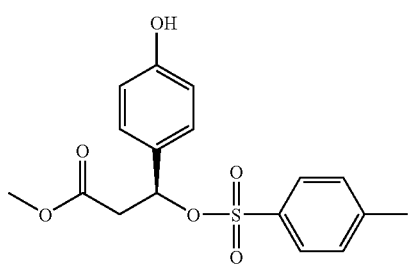

Vc $^1$H NMR (d-DMSO)-δ7.97, d, 2H; δ7.63, d, 2H; δ7.52, d, 2H; δ7.31, d, 2H; δ4.45, dd, 1H; δ3.48, s,3H; δ2.40, s, 3H; δ2.09, t, 2H.

Example 7

To 14.6 gm of compound II and 8 gm of (+)-2-amino-1-butanol was added 150 ml of 2:1 solution of ethanol and water near its boiling point until dissolution just occurs. After cooling, the precipitated salt was collected and dried to yield 13.7 gm of 3(S)-(4-hydroxyphenyl)-3-hydroxy-propionic acid butanol amine salt with 95% ee (enantiomeric excess). The salt was added to a solution of 200 ml of 5% hydrochloric acid in methanol and refluxed for 2 hours and the methanol evaporated under vacuum. 200 ml of methylene chloride and 200 ml of water was added to the residue and the layers separated. The organic layer was evaporated to yield 13.5 gm of 3(S)-(4-hydroxyphenyl)-3-hydroxy-propionic methyl ester (IVa) which was dissolved in 100 ml of p-dioxane and to it was added 26.4 gm of para-toluenesulfonic acid anhydride and 28 ml of triethylamine. The solution was allowed to stir at 45 degrees C. for 1 hr, cooled and evaporated to near dryness. To this residue was added 100 ml of methylene chloride and 100 ml of water and the layers separated. The organic layer was washed with 1N hydrochloric acid and saturated sodium bicarbonate, separated, dried over sodium sulfate and evaporated to yield 15.0 gm of a compound of formula Vc.

$^1$H NMR (d-DMSO)-δ7.97, d, 2H; δ7.63, d, 2H; δ7.52, d, 2H; δ7.31, d, 2H; δ4.45, dd, 1H; δ3.48, s,3H; δ2.40, s, 3H; δ2.09, t, 2H.

Example 8

To 14.6 gm of compound II and 8 gm of (+)-2-amino-1-butanol was added 150 ml of 2:1 solution of ethanol and water near its boiling point until dissolution just occurs. After cooling, the precipitated salt was collected and dried to yield 13.7 gm of 3(S)-(4-hydroxyphenyl)-3-hydroxy-propionic acid butanol amine salt with 95% ee (enantiomeric excess). The salt was added to a solution of 200 ml of 5% hydrochloric acid in methanol and refluxed for 2 hours and the methanol evaporated under vacuum. 200 ml of methylene chloride and 200 ml of water was added to the residue and the layers separated. The organic layer was evaporated to yield 13.5 gm of 3(S)-(4-hydroxyphenyl)-3-hydroxy-propionic methyl ester (IVa) which was dissolved in 150 ml of acetonitrile and to it was added 26.4 gm of para-toluenesulfonic acid anhydride and 28 ml of triethylamine. The solution was allowed to stir at 50 degrees C. for 2 hr, cooled and evaporated to near dryness. To this residue was added 100 ml of methylene chloride and 100 ml of water and the layers separated. The organic layer was washed with 1N hydrochloric acid and saturated sodium bicarbonate, separated, dried over sodium sulfate and evaporated to yield 11.3 gm of a compound of formula Vc.

$^1$H NMR (d-DMSO)-δ7.97, d, 2H; δ7.63, d, 2H; δ7.52, d, 2H; δ7.31, d, 2H; δ4.45, dd, 1H; δ3.48, s, 3H; δ2.40, s, 3H; δ2.09, t, 2H.

Example 9

To 14.6 gm of compound II and 8 gm of(+)-2-amino-1-butanol was added 150 ml of 2:1 solution of ethanol and water near its boiling point until dissolution just occurs. After cooling, the precipitated salt was collected and dried to yield 13.7 gm of 3(S)-(4-hydroxyphenyl)-3-hydroxy-propionic acid butanol amine salt with 95% ee (enantiomeric excess). The salt was added to a solution of 200 ml of 5% hydrochloric acid in methanol and refluxed for 2 hours and the methanol evaporated under vacuum. 200 ml of methylene chloride and 200 ml of water was added to the residue and the layers separated. The organic layer was evaporated to yield 13.5 gm of 3(S)-(4-hydroxyphenyl)-3-hydroxy-propionic methyl ester (IVa) which was dissolved in 100 ml of p-dioxane and to it was added 8.5 gm of acetic anhydride and 28 ml of triethylamine. The solution was allowed to stir at 30 degrees C. for 2 hr, cooled and evaporated to near dryness. To this residue was added 100 ml of methylene chloride and 100 ml of water and the layers separated. The organic layer was washed with 1N hydrochloric acid and saturated sodium bicarbonate, separated, dried over sodium sulfate and evaporated to yield 15.0 gm of a compound of formula Vd.

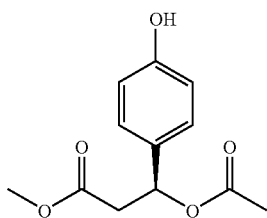

Vd $^1$H NMR-(d-DMSO)-δ7.62, d, 2H; δ7.43, d, 2H; δ4.02, dd, 1H; δ3.48, s, 3H; δ2.12, s, 3H; δ2.04, t, 2H.

Example 10

To 25.9 gm of the compound of formula Vb dissolved in 250 ml of acetone was added 10.8 gm of 4-fluoroaniline and 6.8 gm of sodium iodide. The mixture was refluxed for 8 hours and the acetone was removed under vacuum. The residue was added 200 ml of ethyl ether and washed with saturated sodium bicarbonate, water, separated and evaporated to yield 20.3 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H.

Example 11

To 25.9 gm of the compound of formula Va dissolved in 250 ml of p-dioxane was addedI 11.1 gm of 4-fluoroaniline and 7 gm of sodium iodide. The mixture was refluxed for 8 hours and the acetone was removed under vacuum. To the residue was added 250 ml of ethyl acetate and washed with saturated sodium bicarbonate, water, separated and evaporated to yield 9.0 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H. Example 12

To 25.9 gm of the compound of formula Va dissolved in 250 ml of acetonitrile was added 11.1 gm of 4-fluoroaniline and 7 gm of sodium iodide. The mixture was refluxed for 8 hours and the acetone was removed under vacuum. To the residue was added 200 ml of ethyl ether and washed with saturated sodium bicarbonate, water, separated and evaporated to yield 21.0 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H. Example 13

To 33.4 gm of the compound of formula Vc dissolved in 250 ml of acetone was added 11.1 gm of 4-fluoroaniline and 7 gm of sodium iodide. The mixture was refluxed for 8 hours and the acetone was removed under vacuum. To the residue was added 200 ml of ethyl ether and washed with saturated sodium bicarbonate, water, separated and evaporated to yield 19.0 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H. Example 14

To 22.2 gm of the compound of formula Vd dissolved in 250 ml of acetone was added 11.1 gm of 4-fluoroaniline and 7 gm of sodium iodide. The mixture was refluxed for 8 hours and the acetone was removed under vacuum. To the residue was added 200 ml of methylene chloride and washed with saturated sodium bicarbonate, water, separated and evaporated to yield 7.0 gm of the azetidinone of formula I ($R_1$=para F).

$^1$H NMR-δ7.69, d, 2H; δ7.56, d, 2H; δ7.38, d, 2H; δ7.27, d, 2H; δ3.62, dd, 1H; δ2.14, t, 2H. Example 15

To 25.9 gm of the compound of formula Va dissolved in 250 ml of acetone was added 16.2 gm of 3,4-dichloroaniline and 7 gm of sodium iodide. The mixture was refluxed for 11 hours and the acetone was removed under vacuum. To the residue was added 200 ml of ethyl ether and washed with saturated sodium bicarbonate, water, separated and evaporated to yield 16.9 gm of the azetidinone of formula Ia

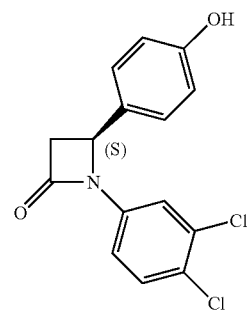

Ia $_1$H NMR-(δ-DMSO) δ7.56, d, 2H; δ7.48, s, 1H; δ7.41, d, 2H; δ7.32, d, 2H; δ3.55, dd, 1H; δ2.09, t, 2H.

I claim:

1. A process for preparing compounds of formula I comprising:
   (a) making an ester IV from 3(S)-(4-hydroxyphenyl)-3-hydroxy-propionic acid wherein $R_2$ is alkyl;

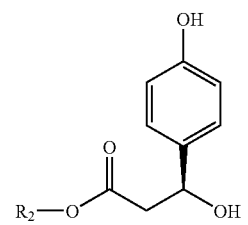

IV (b) activating the alkyl hydroxy group IV by contacting compound IV with an activating agent to form V wherein $R_3$ is selected from the group consisting of alkylcarbonyl, alkylsulfonyl and arylsulfonyl;
   wherein if $R_2$ is methyl then $R_3$ is not methane sulfonyl;

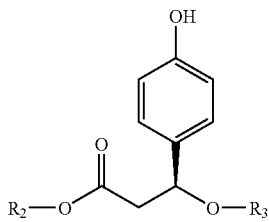

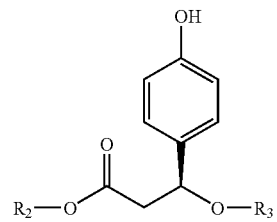

(c) reacting an activated 3(S)-(4-hydroxyphenyl)-3-hydroxy-propionic acid ester derivative V with an aniline; the aniline comprising at least one substituent $R_1$;

wherein $R_1$ is selected from the group consisting of H, halogen, alkyl, O-alkyl, N-dialkyl, S-alky, aryl, and O-aryl;

in the presence of alkali halide and solvent to form a compound of formula I

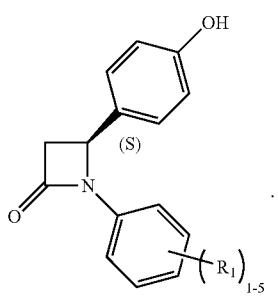

2. The process of claim 1 wherein the ester is made by adding 3(S)-(4-hydroxyphenyl)-3-hydroxypropionic acid to a solution comprising para-toluenesulfonic acid and an alcohol.

3. The process of claim 2 wherein the alcohol is ethanol.

4. The process of claim 1 wherein the activating agent is selected from the group consisting of acetyl chloride, acetyl bromide, acetic acid anhydride, propionyl chloride, propionic acid anhydride, butanoyl chloride, butanoic acid anhydride, pentanoyl chloride, pentanoic acid anhydride, methanesulfonyl chloride, methanesulfonic acid anhydride, para-toluenesulfonyl chloride, para-toluenesulfonic acid anhydride, benzenesulfonyl chloride, benzenesulfonic acid anhydride, para-bromobenzenesulfonyl chloride, para-bromobenzenesulfonic acid anhydride, ethanesulfonyl chloride, and ethanesulfonic acid anhydride.

5. The process of claim 1 wherein $R_1$ is 3,4 dichloro.

6. The process of claim 1 wherein step (c) is performed in a polar aprotic solvent.

7. The process of claim 6 wherein the solvent comprises one or more solvents selected from the group consisting of acetone, 2-butanone, p-dioxane, acetonitrile, and tetrahydrofuran.

8. The process of claim 1 wherein the alkali halide comprises sodium iodide.

9. The process of claim 1 wherein the concentration of alkali halide in solvent is between about 1 mol % and 10 mol %.

10. A compound of formula V wherein $R_2$ is alkyl and $R_3$ is alkylcarbonyl, alkylsulfonyl or arylsulfonyl and wherein if $R_2$ is methyl then $R_3$ is not methanesulfonyl.

11. A compound according to claim 10 wherein $R_2$ is ethyl and $R_3$ is methanesulfonyl.

12. A compound according to claim 10 wherein $R_2$ is methyl and $R_3$ is para-toluenesulfonyl.

13. A compound according to claim 10 wherein $R_2$ is methyl and $R_2$ is acetyl.

14. A process of for preparing compounds of formula I comprising the step of reacting an activated 3 (S)-(4-hydroxyphenyl)-3 -hydroxy-propionic acid ester derivative V with an aniline in the presence of alkali halide and solvent to form a compound of formula I;

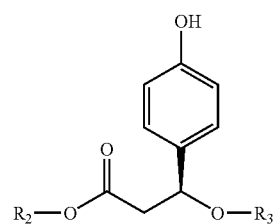

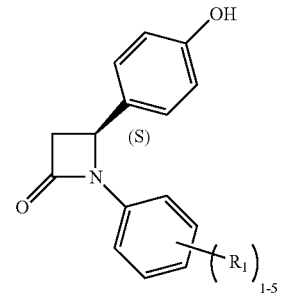

wherein $R_1$ is at least one substituent selected from the group consisting of H, halogen, alkyl, O-alkyl, N-dialkyl, S-alkyl, aryl, and O-aryl;

wherein $R_2$ is alkyl;

wherein $R_3$ is alkylcarbonyl, alkylsulfonyl or arylsulfonyl;

and wherein if $R_2$ is methyl then $R_3$ is not methanesulfonyl.

15. The process of claim 14 wherein the solvent is a polar aprotic solvent.

16. The process of claim 15 wherein the solvent is selected from the group consisting of acetone, 2-butanone, p-dioxane, acetonitrile, and tetrahydrofuran.

17. The process of claim 14 wherein the alkali halide is sodium iodide.

18. The process of claim 14 wherein the concentration of alkali halide in solvent is between about 1 mol % and 10 mol %.

* * * * *